US 6,620,120 B2

(12) United States Patent
Landry et al.

(10) Patent No.: US 6,620,120 B2
(45) Date of Patent: Sep. 16, 2003

(54) METHOD FOR HIGH EFFICIENCY HEMOFILTRATION

(75) Inventors: Donald W. Landry, New York, NY (US); Howard R. Levin, Teaneck, NJ (US); Evan Stuart Garfein, New York, NY (US)

(73) Assignee: Nephros, Inc., New York, NY (US)

( * ) Notice: Subject to any disclaimer, the term of this patent is extended or adjusted under 35 U.S.C. 154(b) by 0 days.

(21) Appl. No.: 09/083,781

(22) Filed: May 22, 1998

(65) Prior Publication Data

US 2001/0003794 A1 Jun. 14, 2001

Related U.S. Application Data

(60) Provisional application No. 60/047,393, filed on May 22, 1997.

(51) Int. Cl.[7] .................... A61M 35/00; A61M 1/00; C02F 1/44; B01D 61/00
(52) U.S. Cl. .................... 604/5.04; 604/5.01; 604/6.09; 604/28; 210/650; 210/321.6
(58) Field of Search .................... 128/898; 604/4–6, 604/4.01, 5.01–5.04, 6.01–6.04, 6.09, 6.1, 6.11, 28–30; 435/2, 3; 422/44, 48; 210/645–47, 650–52, 767, 772, 348, 416.1, 418, 433.1, 434, 500.1, 500.21, 500.23, 321.6

(56) References Cited

U.S. PATENT DOCUMENTS

| | | | |
|---|---|---|---|
| 4,663,058 A | | 5/1987 | Wells et al. ............... 210/801 |
| 4,789,482 A | * | 12/1988 | DiLeo et al. ............... 210/651 |
| 5,108,612 A | * | 4/1992 | Flaig et al. |
| 5,211,849 A | | 5/1993 | Kitaevich et al. ......... 210/645 |
| 5,578,223 A | * | 11/1996 | Bene et al. |
| 5,632,897 A | | 5/1997 | Mathieu .................... 210/645 |
| 5,679,260 A | | 10/1997 | Boos et al. ................ 210/723 |

* cited by examiner

Primary Examiner—Angela D. Sykes
Assistant Examiner—Patricia Bianco
(74) Attorney, Agent, or Firm—Darby & Darby

(57) ABSTRACT

Disclosed herein is an apparatus that efficiently clears solutes from blood of patients with renal disease solely by convection and with a single filter that includes a hemofilter, a blood pump for drawing blood from a patient and propelling the blood into a mixing chamber, a mixing and detention chamber where the blood and a non-isosmotic diluent are mixed and are allowed to approach or reach equilibrium (with regard to solute concentration), a mixing element for creating turbulence in the mixing/detention chamber, and suitable tubing for carrying the pumped blood to and from the patent. Methods for utilizing the apparatus are also disclosed.

15 Claims, 2 Drawing Sheets

METHOD FOR HIGH EFFICIENCY HEMOFILTRATION

This application claims priority from U.S. provisional application Ser. No. 60/047,393 filed May 22, 1997, the disclosure of which is incorporated by reference in its entirety.

BACKGROUND OF THE INVENTION

This invention relates to hemofiltration methods and hemofiltration devices.

When the kidneys in mammalian subjects fail to remove metabolic waste products from the body, many other organ systems also soon fail, unless the subject is provided with a blood-cleansing treatment. The symptoms which develop as a result of metabolic waste buildup are termed uremia and the severity of these symptoms is proportional to the retention in the blood of metabolic waste products ordinarily excreted by the kidneys, two of the markers for toxic waste products bering urea and creatinine. Various other metabolic products, which can accumulate in the bloodstream, include polypeptides, phenols, amines, guanidine, and a variety of middle molecules in the molecular weight range of 500–5000 daltons. The kidneys also provide electrolyte balance in the body when functioning normally, excreting Na+, K+, H+, $Mg^2$, and $Ca^2$, $Cl^-$, $HCO_{3-}$, $PO_4^{-3}$, etc. ions in excess of body needs. When kidney failure occurs, the metabolic waste products will not be excreted and the proper electrolyte balance will not be maintained.

The mechanism the kidney uses for excretion is ultrafiltration, i.e., the formation of a protein-free ultrafiltrate of plasma by means of a hydrostatic pressure versus oncotic pressure gradient that extrudes water and any dissolved small and middle-sized molecules through a semipermeable membrane. This extrusion retains cells and larger proteins in the blood and thereby permits the convective clearance of waste, salts, and ions. In the kidney, the ultrafiltration is followed by partial reabsorption of useful components and excretion of the remainder. Hemodialysis has been routinely available to subjects in renal failure for about the last 30 years and has permitted maintenance of individual patients for decades, often until death (not resulting from renal failure) or until renal transplantation. In contrast to the ultrafiltration mechanism utilized by the kidneys, hemodialysis (dialysis of the blood outside of the body) removes solutes, such as creatinine and urea, from the blood by diffusion down a concentration gradient through a semipermeable membrane. The solutes diffuse across a semipermeable membrane into a second liquid called dialysate. This principle of clearance by diffusion has remained the cornerstone of therapy for kidney failure for the last 30 or so years. To the extent that there have been technical advances they have occurred in the areas of increased blood flow, increased dialysate flow, improved filter characteristics and dialysate composition.

"High efficiency hemodialysis" is a variant of hemodialysis in which high blood flow rates and high dialysis flow rates are utilized to increase solute clearance. Despite the achievement of high Blood Urea Nitrogen (BUN) clearances from the subject's blood, high-efficiency dialysis has significant drawbacks. First, this type of treatment is unable to clear so-called "middle molecules" from the blood. Middle molecules, as indicated previously, are those with a molecular weight of between 500 and 5000 daltons, and include molecules such as $\beta_2$-microglobulin. The accumulation of $\beta_2$-microglobulin in the blood of patient on long-term hemodialysis is responsible for the incidence of amyloidosis, one of the major sources of morbidity in subjects suffering from renal failure undergoing dialysis. Second, the time for treatment is still considerable. The best dialysis centers, using the most advanced equipment, dialyzing the leanest, most fit patients report, at best, successful treatment times of three hours and the average time is 3.5 hours. The reason for the failure to decrease treatment time further is that patients who undergo rapid hemodialysis report discomfort, not infrequently profound, during and after dialysis treatments. During dialysis, solutes have the opportunity to pass both out of and in to the blood. This occurs because the primary motive force in dialysis is diffusion down a concentration gradient, i.e., diffusion from a compartment of high solute concentration to a compartment of low solute concentration. While current technology provides for highly sterile and relatively pyrogenfree hemodialysis filters and filter cartridges, it is likely that hemodialysis filters and filter cartridges contain traces of compounds which dissolve in the dialysate and diffuse across the filter membrane, into the blood contributing to the discomfort that subjects undergoing dialysis frequently experience.

Convection, the natural mechanism for the renal clearance of solutes from the blood, has been previously employed in dialysis but not fully utilized. Standard hemodialysis uses convection through the process of ultrafiltration, to a very limited degree (only in the context of concomitant diffusion, which provides 99% of the solute clearance), and mainly as a means to reduce interdialysis weight gain. Whereas solute clearance by diffusion is based upon the movement of particles due to the force generated by the concentration gradient of the particles across a semipermeable membrane, convection is based on the movement of particles due to the force generated by the bulk flow of the solvent in which the solute is dissolved. Prior to the present invention, convection had only been used as a minor component in the clearance of solute in standard hemodialysis therapies because any significant degree of bulk flow of water out of the blood compartment will necessarily concentrate the protein constituents of the blood and the resulting increase in oncotic pressure will retard further ultrafiltration. IN addition, concentrating the plasma proteins can promote clotting. These difficulties have been considered by those in the art to be major impediments to large volume hemofiltration ins subjects with end-stage renal disease.

The development of large-pore, high flux blood filters has enabled so-called "high flux hemodiafiltration." With this method, convection occurs early during the transit of blood through the highly porous filter, i.e., in the part of the filter nearest the blood inlet. Later in the blood's transit, diffusion clearance predominates, but overall, convection is still a relatively minor component of the solute clearance per treatment. The approximate convection/diffusion ratio with this method, as currently practiced, is approximately 30%, i.e., 30/100.

Hemofiltration refers to the exclusive use of ultrafiltration to convectively clear solutes. A method that uses hemofiltration exclusively for clearing solutes prevents any back-diffusion of plasticizers from filter to blood, thereby avoiding or significantly ameliorating the discomfort that most dialysis subjects experience during and after dialysis. However, in the hemofiltration methods of the prior art the problem of low filtration rates due to the excessive concentration of plasma proteins has resulted in inadequate solute clearance. Predilution, i.e., dilution of the blood before filtration with a volume of an isosmotic solution, has rarely been used in hemofiltration due to the requirement for large volume delivery. An attempt has been made to address the problem of low solute clearance efficiency by the use of multiple filters with post-filter dilution, but the increased equipment and treatment costs associated with use of multiple filters have effectively eliminated this mode of treatment from being used in the United States. Thus, there is a need in the art for a high efficiency hemofiltration device that can function with one filter and that can achieve rapid (i.e., faster) solute clearance from the blood with at least the same efficiency as currently used hemodialysis methods, or that can achieve higher levels of solute clearance in the same treatment time as the systems and devices currently in use. The art is also in need of a hemofiltration system and device that are effective in clearing so called "middle molecules" from a "patient's blood."

SUMMARY OF THE INVENTION

A method and apparatus have now been unexpectedly discovered the efficiently, and with a single filter, clear solutes from the blood of renal disease patients solely by convection. The method comprises the steps of 1. diluting and mixing the blood to be cleared of solute with a non-isosmotic solution;
2. delaying entry of the blood-diluent mixture into the filtering means for a sufficient amount of time to allow diffusion/transport of solutes from the red blood cells in said blood; and
3. filtering the blood-diluent mixture through a single filter means comprising a highly porous membrane, providing for rapid and efficient solute clearance, including clearance of "middle molecules" for which dialysis is not effective.

It has now unexpectedly been discovered that mixing blood with a non-isosmotic diluent and allowing the blood to equilibrate with the non-isosmotic diluent is a mixing/detention chamber allows solutes to be transferred from inside the red blood cells of the blood to the plasma/diluent. This increases the effective concentration of solutes in the blood/diluent system that can be cleared by convection, allowing for greater solute clearance from blood in a shorter time period. Further, the red blood cells, after having lost through diffusion or transport quantities of solutes due to equilibration with the non-isosmotic diluent, can then be sent back into the body of the patient, where they can serve as solute "sponges," loading up with solutes present in the subject's blood which will again be extruded the next time the blood cell goes through the hemofiltration apparatus of the invention. These features of the present invention, i.e., causing extrusion of solutes from red blood cells and utilizing red blood cells that have equilibrated with non-isosmotic diluent, overcome the principal deficiency of hemofiltration of blood reported in the prior art, namely the relatively inefficient solute clearance relative to dialysis. Thus, the present invention provides a method for cost and time efficient hemofiltration, with superior results as compared to dialysis, while employing only a single filter.

In a preferred embodiment, the apparatus of the present invention includes a hemofilter, a blood pump for drawing blood from a patient and propelling the blood into a mixing chamber, a mixing and detention chamber where the blood and a non-isosmotic diluent are mixed and are allowed to approach or reach equilibrium (with regard to solute concentration), a mixing element for creating turbulence in the mixing/detention chamber, and suitable tubing for carrying the pumped blood to and from the patient. The system further includes a system for continuous mixing of water and concentrate of diluent thereby maintaining a supply of non-isosmotic diluent, and a diluent pump for pumping the diluent to the appropriate blood tubing access port. Fluid from the hemofilter is moved by pump to waste drainage. The apparatus also contains flow meters for monitoring the flow of fluid into and out of the patient, a line to waste drainage, a mixing chamber, a back pressure valve for controlling the transmembrane pressure in the filter, and a controller operably connected to the blood pump, the diluent pump, and the drainage pump. Also part of the apparatus are means for controlling and determining the amount of diluent added to the subject's blood and a means for determining the amount of fluid drained from the hemofilter.

The advantages of the apparatus and method of the present invention are achieved at least in part as the result of prediluting the blood to be treated with a non-isosmotic diluent, which provides for increased diffusion and/or transport of solutes from red blood cells, and from the presence and use of a mixing/detention chamber, which allows for solute efflux from the intracellular compartment of red blood cells to the blood plasma/diluent extracellular compartment. These features of the invention permit hemofiltration of blood to be performed in the same or less time than is required for adequate solute removal by dialysis, while maintaining the economy of using a single filter cartridge, and avoiding the recognized intra- and post-treatment side effects of hemodialysis. Further features and advantages of the system and apparatus of the present invention will become apparent with reference to the drawings and the detailed description which follows.

DETAILED DESCRIPTION OF THE INVENTION

Figure 1:
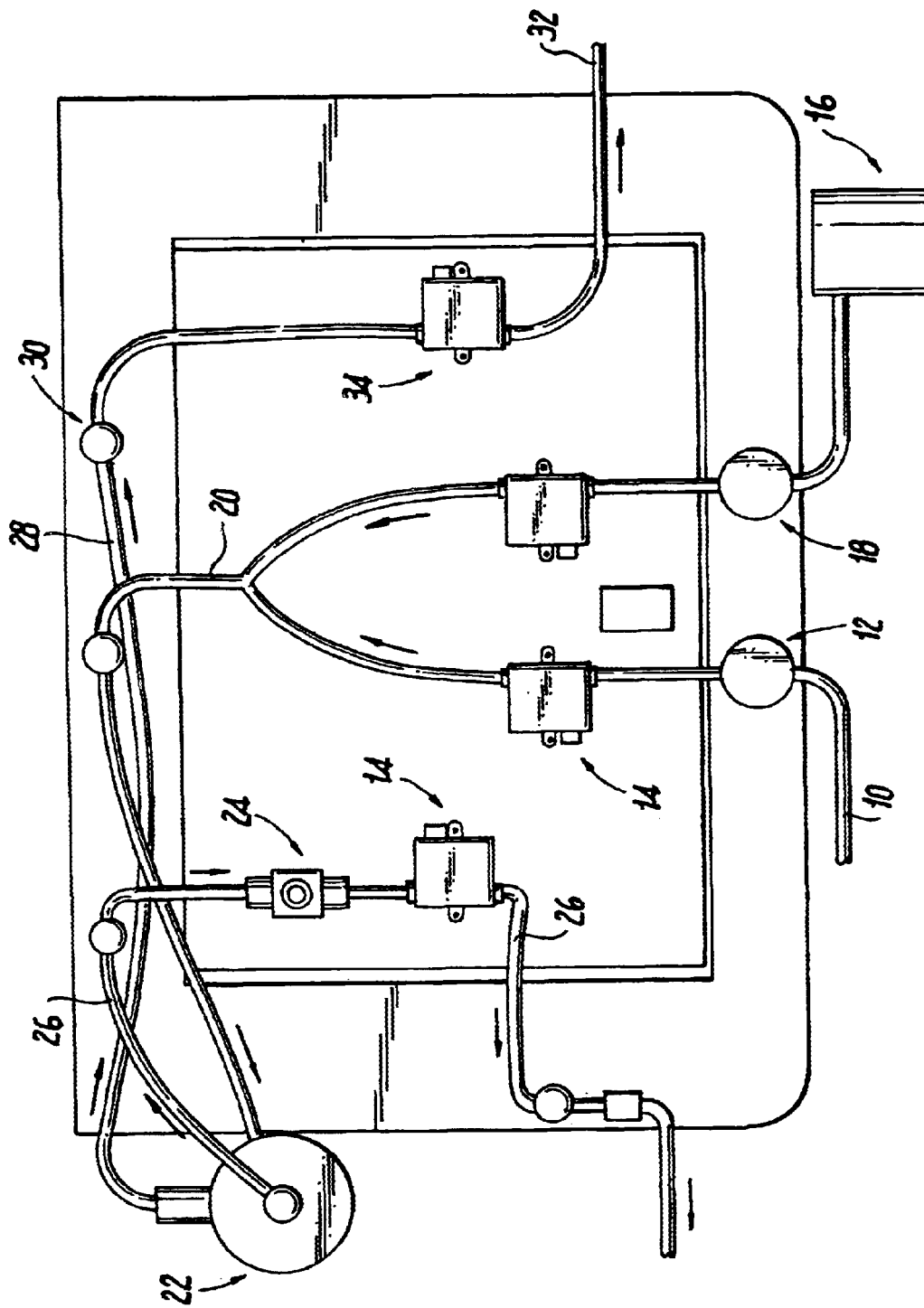
FIG. 1 is a diagrammatic representation of one embodiment of the system of the present invention.
Figure 2:
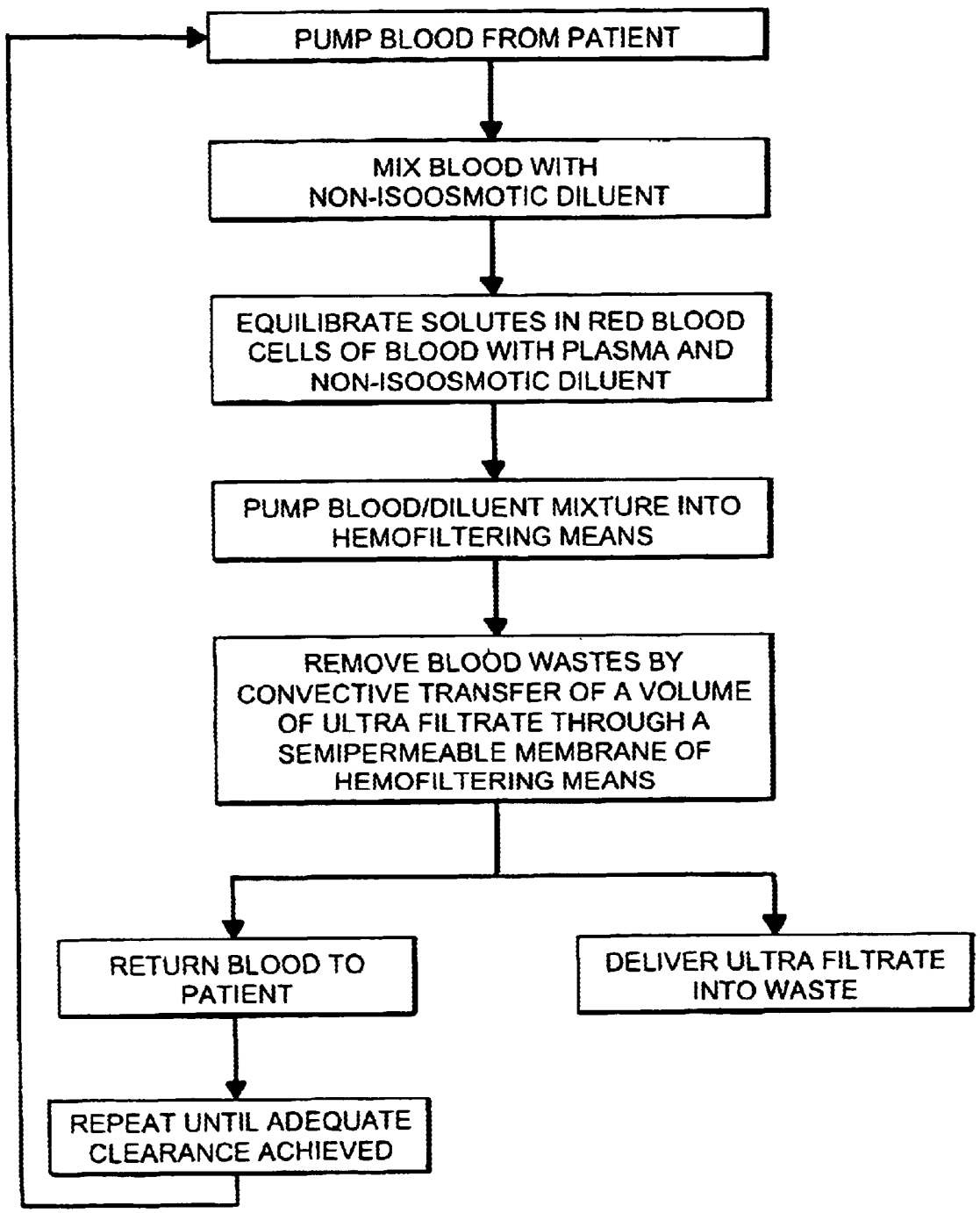
FIG. 2 is a flow chart illustrating the method of the present invention.

FIG. 1 is a diagrammatic representation of a preferred embodiment of the apparatus of the present invention.

In operation, blood is pumped from a patient (not shown) afflicted with renal disease of insufficiency, which may be an adult, pediatric or neonatal patient, through a suitable catheter (not shown) and input tubing 10 by means of a blood pump 12. Suitable blood pumps include standard clinical grade roller pumps such as the Stockert-Shiley model 10-00-00. To be useful in the present invention, a pump must be capable of delivering and sustaining consistent flow rates of between about 100 and about 100 ml/min. Roller head pumps have been found to be particularly useful in practicing the invention, as well as those pumps customarily employed in currently available hemodialysis devices. Since there are no cellular components in the diluent or the utlrafiltrate, the invention is not limited to use with roller pumps and other pumps such as, for example, piston or diaphragm pumps may also be employed.

Suitable types of tubing for use in the apparatus of the present invention include the flexible plastic tubing offered under the designation Tygon by the Norton Company or Pharm Med tubing from the Norton Company. However, the standard tubing (polyvinylchloride) used in prior art dialysis devices to conduct blood through the dialysis apparatus is preferred. Input tubing 10 through which the patient's blood is pumped preferably includes a flow meter 14 upstream of pump 12. A preferred flow meter that has been employed in the present invention is made by Transonics Inc. of Ithica.

Concurrently with the withdrawal of blood from the patient, a non-isosmotic diluent fluid is pumped from reservoir 16 into tubing 10 by diluent pump 18. The diluent fluids employed in practicing the present invention are electrolytically balanced aqueous solutions that are mildly basic. The non-isosmotic diluent can be derived from a standard dialysis fluid concentrate such as concentrate solution for acetate dialysis, manufactured by Dial Medical Supply, and the like, which comprises an aqueous solution of sugar and electrolyte salts constituted to yield a isosmotic solution upon 1:34 dilution (e.g. sodium 140 mM, and dextrose 200 mg percent). This fluid can be diluted to be either hypertonic or hyptonic relative to blood plasma. Alternatively, the diluent can be a bicarbonate dialysate (isosmotic) which contains the same electrolytes with two exceptions, (1) no calcium is present, and (2) bicarbonate is employed instead of acetate. To create a preferred hypertonic diluent, the concentrate is diluted 17-fold to yield a final solution of sodium 280 mM, calcium 6 mM, potassium 4 mM, chloride 216 mM, acetate 38.5 mM, dextrose 400 mg percent. In an alternative hypertonic diluent based mainly on an increase in dextrose concentration, the concentration of dextrose is doubled by adding a 50% dextrose solution and sodium is increased 5% by adding a sodium chloride solution, respectively, to the concentrate which is diluted 1:34. To make the dialysate hypotonic, the concentrate would be diluted 1:68 to yield concentrations: sodium 75 mM, potassium 1 mM, magnesium 0.75 mM, calcium 1.5 mM, chloride 54 mM.

The patient's blood and the diluent are then mixed, in a controlled manner, in mixing/detention chamber 20. The blood/diluent mixture is retained in the mixing/detention chamber for a period of time defined by the flow rate of the blood and diluent and the volume of the mixing/detention chamber.

The blood/diluent mixture flows through hemofilter 22. The filter 22 is generally composed of bundled fibers which may in some instances be hollow. One suitable filter for use in the invention is made of polysulfone fibers. Filters suitable for use in the system of the present invention are readily available; examples of suitable hemofilters are the Fresenius F80 high flux, high ultrafiltration coefficient cartridge (which has an ultrafiltration coefficient of 55 ml/hour/mm of mercury) and the Diafilter manufactured by AMICON, Danvers, Mass. However, hemofiltration filters composed of fibers made of cellulose acetate, polyacrylonitrile and polyamide having ultrafiltrating coefficients of between 40 and 60 ml/hour/mm of mercury or greater may be employed in the invention.

When a hypotonic diluent is employed, a balancing quantity of hypertonic diluent must be added after passage through the filter. The balancing quantity of hypertonic diluent should have the same proportion of ions, but at a higher concentration, such that after allowing for the amount of material lost through the ultrafiltration step, the net result will be to return the blood to the patient in an isosmotic state.

For the hypertonic diluent, an analogous hypotonic balancing diluent would be added after passage through the filter unless hypertonicity is achieved, in a preferred embodiment, mainly through the sue of an increased glucose concentration. However, since such glucose would be metabolized in viva, no hypotonic diluent need be added after the filter and the filtered blood is returned to the patient where the sugar is metabolized. The 145 mM sodium concentration is an acceptable level of the hypertonic diluent since renal dialysis candidates tend to be hypotonic.

Backpressure valve 24 is in fluid connection with output tubing 26 through which blood flows out of hemofilter 22.1 Switches and valves of the type used in present hemodialysis machines can be employed as switches and valves in practicing the present invention. Output tubing 26 includes a second flow meter 14 slightly upstream of backpressure valve 24. The patient's blood exits hemofilter 22, passes through backpressure valve 24 and output tubing 26 and is returned to the patient via any suitable means such as a venous catheter arrangement (not shown). Also preferably provided is a means for eliminating any bubbles in the blood before it is returned to the patient as standard practice.

Upon passage of the blood/diluent mixture through the hemofilter, an ultrafiltrate containing waste solutes and "middle molecules" will pass through the semipermeable membrane of the filter. The primary waste solutes in the ultrafiltrate include creatinine, urea and phosphate. Among the middle molecules removed by the hemofiltration method of the invention are of $\beta_2$-microglobulin, whit a molecular weight of about 11,800. Dialysis methods have not been able to clear such middle molecules, because standard dialytic therapy becomes increasingly inefficient at higher molecular weights. The ultrafiltrate is pumped from hemofilter 22 through ultrafiltrate outlet tubing 28 by means of drain pump 30, which is preferably a roller-type pump, and may be the same as diluent pump 18. Ultrafiltrate output tubing 28 preferably includes a flowmeter 34 downstream of hemofilter 22 and pump 30. Ultrafiltrate pumped from hemofilter 22 is pumped into waste drainage line 32.

Backpressure valve 24 regulates the convective force due to blood pressure on the membrane of the hemofilter. The convective force across the membrane can, alternatively or in addition, be adjusted by regulating the rate of flow of the ultrafiltrate through drain pump 30. By impeding the flow of ultrafiltrate, e.g., by pumping more slowly than the rate of ultrafiltration, pressure is increased in hemofilter cartridge 22 and convection of ultrafiltrate from the blood/diluent mixture is opposed, and so slows. By producing negative pressures, i.e., a slight vacuum, in hemofilter cartridge 22 outside of the membrane filaments, transmembrane pressure is increased an convection is accelerated. The amount of ultrafiltrate can be modified by regulating the pressure outside of the membrane filaments. This feature of the invention allows the volume of blood to be returned to the patient to be adjusted.

The methods of the present invention provide for rapid and efficient solute clearance from blood, including clearance of "middle molecules" for which dialysis is not effective. The hemofiltration method of the invention utilizing the hemofiltration device of the invention generally comprises the steps of:

(a) pumping blood from the bloodstream of a patient:
(b) mixing the blood of the patient with a non-isosmotic diluent, which may be either hypotonic or hypertonic;
(c) equilibrating the solutes in the red blood cells of the patient's blood with a solution comprising the patient's blood plasma and the non-isosmotic diluent, thereby increasing the concentration of waste solutes in the plasma/diluent mixture;
(d) pumping the blood/diluent mixture into a hemofiltering means, and removing blood wastes by convective transfer of a volume of blood plasma/diluent mixture, i.e., ultrafiltrate, through the semipermeable membrane of the hemofiltering means;
(e) conducting the blood into the blood outlet tubing and back into the patient; and
(f) delivering the ultrafiltrate into the waste outlet tubing and subsequently into the ultrafiltrate reservoir.

In practicing the method of this invention, the non-isosmotic diluent can be hypertonic or hypotonic relative to the blood plasma of the patient. Such diluents will, when hypotonic have, for example, a calcium concentration as low as 1.5 meq/l; magnesium concentration as low as 0.75 meq/l; acetate concentration as low as 19.25 meq/l, chloride concentration as low as 54 meq/l; dextrose concentration as high as 400 mg percent; calcium concentration as high as 6 meq/l; magnesium as high as 3 meq/l and acetate concentration as high as 77 meq/l; and the chloride concentration as high as 216 meq/l.

In practicing the method of the invention, the blood flow rate from the patient is maintained at between about 250 ml/min and about 400 ml/min, preferably between about 300 ml/min and about 350 ml/min.

Generally, between about 400 ml and about 800 ml of diluent will be added per 250 ml of blood which enters the hemofiltration apparatus, preferably between about 500 and 600 ml of diluent per 250 ml of blood.

The rate of mixed blood/diluent flow through the hemofiltering means is maintained at a rate between about 650 ml/min and about 1,200 ml/min, preferably between about 800 ml/min and about 950 ml/min.

It is contemplated that the average time to dialyze a human patient will be between about 150 minutes and 180 minutes, using the method and apparatus of the invention. This time period is less than the time required for present dialysis technologies to achieve equivalent solute clearance. Alternatively, the apparatus and method of the invention can achieve greatly improved clearance levels (i.e., reduced levels of plasma urea, phosphates and creatinine) in the same dialysis time period as prior art techniques.

Ultrafiltrate is produced at a rate of between about 400 ml/min and 850 ml/min, preferably between about 500 ml/min and abut 650 ml/min.

In order to achieve this rate of ultrafiltration production, pressure across the semipermeable membrane of the hemofiltration means is maintained at between about 400 mM Hg and about 600 mM Hg. This pressure gradient is maintained and modified by altering the flow rate of blood/diluent mixture out of the hemofiltration means by adjusting the backpressure valve (24) and by providing negative pressure on the outlet tubing side of the semipermeable membrane of the filtration means. In treating a patient with chronic renal failure, plasma volume regulation is an essential component of treatment. By producing a larger volume of ultrafiltrate by convection than the volume of diluent added, it is possible to contract a patient's plasma fluid volume. By forming ultrafiltrate at a rate of about 25 ml/min greater than the rate wet which diluent is added, it is possible to reduce a patient's weight by 3 kilograms in a 120 minute treatment.

Non-isosmotic diluent can either be made, sterilized, and stored prior to practicing the hemofiltration methods of the present invention, or it can be prepared concurrently by diluting a solution between 68-fold and 17-fold more concentrated than the previously defined hypoosmolar and hyperosmoloar diluent solutions. Filtered water is continuously mixed with the concentrated hyperosmolar and hypoosmolar diluent at a rate such that the final concentration of diluent is respectively hypoosmotic or hyperosmotic relative to blood plasma is obtained. The solution is then filtered in line in order to remove bacteria and particulate matter. The total volume of diluent to treat a typical 70 kg male is between about 60 and 120 liters, preferably between about 60 and 80 liters.

The blood/diluent mixture will generally be detained or resident in the mixing chamber for between about 10 and 60 seconds, preferably for between about 20 and 40 seconds. During this time, solutes to be cleared move from the red blood cells into the diluent fluid as a function of the change in red cell volume. The mixing chamber will generally have a volume of between about 100 ml and about 1,200 ml. This period represents the largest volume that can be safely sequestered in the mixing chamber. The blood and diluent meet at the top of a T and mix by turbulence. The blood then passes through the vertical body of the T (which has a variable volume which is variable and sufficient to delay the transit of blood, from the initial mixing to entrance into the dialysis cartridge or filter for between about 10 and 60 seconds). In current animal experiments where the blood flow is 200 cc/min and the diluent flows at 200 cc/min, the total flow entering the filter is 400 cc/min. Thus, as a non-limiting example, the volume of the chamber would have to be 400 cc to impart a 60-second delay. This chamber is an adequate size for use with human adults, but for dog experiments and anticipated pediatric use of a small size chamber is required. An exemplary mixing device sold by Cole Parmer under the trademark Pulse Dampener by Masterflex E-07596-20 and has a 175 ml capacity; this device was modified to allow flow of both diluent and blood to enter the chamber. The mixing device creates a turbulent flow due to the opposing flow of blood and diluent; however, other means of mixing blood with non-isosmotic diluent to create a turbulent flow effect can be employed.

After hemofiltration treatment according to the present methods, the BUN clearance from the blood of the treated patient will be at least about 180, preferably about 270 ml/min. Creatinine clearance will be at least about 130, and preferably about 200 ml/min. $\beta_2$-microglobulin (a "middle molecule") clearance will be at least 100 and preferably about 150 ml/min.

The present invention will now be further described in the following non-limiting, illustrative examples. While this invention has been described with reference to its preferred embodiments, other embodiments can achieve the same result. Variations and modifications of the present invention will be obvious to those skilled in the art an it is intended to cover in the appended claims all such modifications and equivalents as fall within the spirit and scope of this invention.

EXAMPLES

Example 1

In Vitro Trial

A test fluid containing 10 liters of citrated bovine blood was loaded with urea, creatinine, and Vancomycin and allowed to equilibrate for one hour. The starting concentrations of these molecules were: blood urea nitrogen (BUN) avg 114 mg/dl, creatinine (Cr) avg 30 mg/dl, and Vancomycin 56 mg/l. Variation reflects the range of concentrations face in the clinical setting. IN testing for the ability of a hemofiltration system to clear "middle molecules," Vancomycin is generally employed as a representative "middle molecule" since it is readily available and has an appropriate molecular weight. These experiments were run at constant flows, and there was a consistent decline in the flow across the filter after about 30 minutes of running time. After 120 minutes of filtering using the apparatus and method of the present invention and a diluent comprising of sodium 140 meq/l, calcium 3 meq/l, potassium 2 meq/l, magnesium 1.5 meq/l, chloride 108 meq/l, acetate 38.5 meq/l and dextrose 200 mg percent, the average blood levels were BUN-44 mg/dl, Cr-10 mg/dl, Vancomycin-24 mg/l. This experiment establishes that the present invention successfully clears BUN, Cr and Vancomycin from blood, with a relatively short period of dialysis treatment.

Example 2

In Vivo Trial

The in vivo trials were run in the same fashion as for the in vitro trials. Mongrel dogs underwent bilateral ureteral ligation on day 1. On day three, their bloods were analyzed for evidence of uremia. They were then dialyzed for 120 minutes using the apparatus and method of the present invention. The diluent employed had the following composition: sodium 140 meq/l, calcium 3 meq/l, potassium 2 meq/l, magnesium 1.5 meq/l, chloride 108 meq/l, acetate 38.5 meq/l and dextrose 200 mg percent. The dialysis was carried out by implanting arterial and venous catheters in the femoral vessels of each animal. After priming the circuit, flow was initiated.1 In the two dogs dialyzed, the post-dialysis BUN dropped from an average of 116 mg/dl to an average of 68 mg/dl. Creatinine was reduced from 7.8 mg/dl to 4.3 mg/dl and Vancomycin reduced from 29 mg/l to 10.4 mg/l.

This trial illustrates that the apparatus and method of the present invention can clear high levels of blood impurities (including "middle molecules") in a relatively short dialysis time period.

What is claimed is:

1. A method for hemofiltering blood from a subject comprising:

(a) admixing blood from said subject and a non-isosmotic diluent, thereby producing a blood-diluent mixture;

(b) retaining said blood-diluent mixture in a mixing chamber for a period of time sufficient to cause a predetermined rate of transfer of solutes from blood cells in said blood-diluent mixture to the non-isosmotic diluent prior to introducing the blood-diluent mixture to a filtering device, said time period being sufficient to permit the blood to substantially equilibrate with the non-isosmotic diluent prior to the mixture being introduced into the filtering device; and (c) ultrafiltering said blood-diluent mixture in the filtering device.

2. The method of claim 1 and further comprising:

(d) returning said hemofiltered blood-diluent mixture to said patient; and (e) repeating steps (a) through (c) until a predetermined level of solutes has been cleared from said blood.

3. A method according to claim 2 wherein said solutes comprise at least one solute selected from the group consisting of urea, creatinine and phosphate.

4. A method according to claim 3 wherein said time period is between 10 and 60 seconds.

5. A method according to claim 4 wherein said time period is between 20 and 40 seconds.

6. A method according to claim 2 wherein said time period is between 10 and 60 seconds.

7. A method according to claim 6 wherein said time period is between 20 and 40 seconds.

8. The method of claim 1 wherein said non-isosmotic diluent comprises a bicarbonate solution.

9. A method according to claim 8 wherein said time period is between 10 and 60 seconds.

10. A method according to claim 9 wherein said time period is between 20 and 40 seconds.

11. A method according to claim 1 wherein said time period is between 10 and 60 seconds.

12. A method according to claim 11 wherein said time period is between 20 and 40 seconds.

13. The method of claim 1 wherein said non-isosmotic diluent comprises an acetate solution.

14. A method according to claim 13 wherein said time period is between 10 and 60 seconds.

15. A method according to claim 14 wherein said time period is between 20 and 40 seconds.

* * * * *